United States Patent
Mesters

(10) Patent No.: US 7,297,655 B2
(45) Date of Patent: Nov. 20, 2007

(54) CATALYST AND ITS USE IN DESULPHURISATION

(75) Inventor: Carolus Matthias Anna Maria Mesters, Amsterdam (NL)

(73) Assignee: Shell Oil Company, Houston, TX (US)

( * ) Notice: Subject to any disclaimer, the term of this patent is extended or adjusted under 35 U.S.C. 154(b) by 662 days.

(21) Appl. No.: 10/668,908

(22) Filed: Sep. 23, 2003

(65) Prior Publication Data

US 2004/0102317 A1    May 27, 2004

(30) Foreign Application Priority Data

Jun. 2, 2001   (FR) .................... 01 08157
Sep. 23, 2002  (EP) .................... 02256589

(51) Int. Cl.
*B01J 23/755* (2006.01)

(52) U.S. Cl. ............... 502/337; 502/300; 502/325; 502/328; 502/329

(58) Field of Classification Search ............. 502/337
See application file for complete search history.

(56) References Cited

U.S. PATENT DOCUMENTS 5,094,996 A    3/1992  Kidd ................. 502/405
5,306,685 A    4/1994  Khare ................ 502/253
6,193,877 B1   2/2001  McVicker et al. ..... 208/217
6,254,766 B1   7/2001  Sughrue et al. ...... 208/244

FOREIGN PATENT DOCUMENTS

EP   0401788 A1   12/1990
EP   1224970 A1    7/2002

OTHER PUBLICATIONS

"New Hydrodesulfurization Catalyst for Pertroleum-Fed Fuel Cell Vehicles and Cogenerations," by Kinya Tawara, Takeshi Nishimura, Hikoichi Iwanami, Tokuyoshi Nishimoto, and Takashi Hasuike, *Ind. Eng. Chem. Res.* 2001, 40, pp. 2367-2370.

*Primary Examiner*—Tam M. Nguyen
(74) *Attorney, Agent, or Firm*—Charles W. Stewart

(57) ABSTRACT

A catalyst is provided comprising nickel in a reduced valence state on a carrier comprising zinc oxide and alumina, wherein the Zn:Ni atomic ratio is at least 12, and the catalyst particles are prepared by a) mixing zinc oxide in the form of a powder and alumina or an alumina precursor in the form of a powder; b) peptising the powder mixture and forming an extrudable dough by adding acid and water to the powder mixture in such amounts that the dough contains 0.8-1.2 moles acid equivalents per kg powder; c) extruding the extrudable dough to form extrudates; d) drying and calcining the extrudates; e) impregnating the extrudates with an aqueous solution of a nickel compound; f) drying, calcining and reducing the impregnated extrudates.

26 Claims, No Drawings

CATALYST AND ITS USE IN DESULPHURISATION

FIELD OF THE INVENTION

The present invention relates to catalyst comprising nickel on a carrier, and to a process for desulphurisation of a hydrocarbonaceous feedstock using such catalyst.

BACKGROUND OF THE INVENTION

Catalytic processes that are used for the conversion of hydrocarbonaceous streams into a hydrogen-rich gas, e.g. steam reforming, autothermal-reforming, and catalytic partial oxidation, are extremely sensitive to sulphur. Desulphurised hydrocarbonaceous streams that are obtained after conventional hydrodesulphurisation processes using Co—Mo or Ni—Mo catalysts generally have a too high sulphur level to be suitable for these sulphur-sensitive applications. Hydrodesulphurised hydrocarbonaceous streams contain sulphur compounds that are difficult to remove, such as heterocyclic sulphur compounds like thiophenes, benzothiophenes, substituted and condensed ring dibenzothiophenes. Therefore, there is a need for catalysts that are able to remove the small amount of "difficult" sulphur compounds that are still present in hydrocarbonaceous streams that have undergone a conventional hydrodesulphurisation.

Catalysts containing nickel, zinc oxide and alumina have been reported for deep desulphurisation of hydrocarbon streams, i.e. to sulphur concentrations as low as 0.1 ppm. Generally these catalysts have a double function: nickel catalyses the reaction of sulphur with hydrogen to form hydrogen sulphide and zinc oxide absorbs the hydrogen sulphide formed by reaction to zinc sulphide and water. Alumina is needed for the strength of the catalyst particles and it creates a relatively high specific surface area which is needed for a good nickel dispersion. These catalysts are able to remove heterocyclic sulphur compounds.

In EP 1 224 970 for example, such a double function catalyst for the deep desulphurisation of kerosene is described. The catalyst has 5-25 wt % Ni, 30-70 wt % ZnO and the remainder alumina. The catalyst is prepared by precipitating a water-soluble nickel salt and a water-soluble zinc salt in a basic solution, admixing alumina or an alumina precursor with the precipitate and calcining the admixture.

In Ind. Eng. Chem. Res. 40 (2001) p. 2367-2370, a similar double function catalyst comprising nickel, zinc oxide and alumina is described. The Zn:Ni ratio of the described catalysts is below 12.

In U.S. Pat. No. 6,254,766, a sorbent composition for the removal of "difficult" sulphur compounds is disclosed. The sorbent composition comprises zinc oxide, silica, alumina and nickel in a substantially reduced valence state. The sorbent preferably contains 15-60 weight % zinc oxide and 15-40 weight % nickel. The exemplified catalyst has a Zn:Ni ratio far below 12. A process for the removal of organosulphur from a stream of cracked-gasoline or a diesel fuel using this sorbent composition is described. After contacting the stream with the sorbent composition, the sorbent composition is regenerated by reducing it in an activation zone.

SUMMARY OF THE INVENTION

A catalyst comprising nickel in a reduced valence state on a carrier comprising zinc oxide and alumina, wherein the Zn:Ni atomic ratio is at least 12, and the catalyst is prepared by:

mixing zinc oxide in the form of a powder and alumina or an alumina precursor in the form of a powder thereby providing a powder mixture;

peptising the powder mixture and forming an extrudable dough by adding acid and water to the powder mixture in such amounts that the dough contains 0.8-1.2 moles acid equivalents per kg powder thereby providing an extrudable dough;

extruding the extrudable dough to form extrudates;
drying and calcining the extrudates;
impregnating said calcined extrudates with an aqueous solution of a nickel compound thereby providing an impregnated extrudate;
drying, calcining and reducing the impregnated extrudates.

A process for desulphurisation of a hydrocarbonaceous feedstock, comprising contacting the feedstock with the catalyst described above in the presence of hydrogen, at a temperature in the range of from about 150 to about 500° C., a pressure in the range of from about 1 to about 50 bar (absolute), and a liquid velocity in the range of from about 0.1 to about 50 kg feedstock/litre catalyst/h.

DETAILED DESCRIPTION OF THE INVENTION

The present invention relates to catalyst particles comprising nickel in a reduced valence state on a carrier comprising zinc oxide and alumina, and to a process for desulphurisation of a hydrocarbonaceous feedstock using such catalyst particles.

It would be advantageous to increase the amount of ZnO, since this would enhance the hydrogen sulphide absorbing capacity of the catalyst and thus increase the lifetime of the catalyst before regeneration or replacement is needed. An increase in zinc oxide, however, will result in a decrease in alumina content and thus in a decrease in strength and/or nickel dispersion.

The aim of the present invention is to maximise the sulphur absorbing capacity of a nickel/zinc oxide/alumina catalyst whilst having sufficient catalytic conversion activity for "difficult" sulphur compounds and having sufficient strength to use the catalyst in an industrially-sized reactor.

It has now been found that it is possible to prepare strong catalyst particles with a Zn:Ni ratio of at least 12 and with sufficient catalytic conversion activity for "difficult" sulphur compounds, by preparing them in a specific way.

Accordingly, the present invention relates to a catalyst (catalyst particles) comprising nickel in a reduced valence state on a carrier comprising zinc oxide and alumina, wherein the Zn:Ni atomic ratio is at least 12, and the catalyst particles are prepared by:
mixing zinc oxide in the form of a powder and alumina or an alumina precursor in the form of a powder;
peptising the powder mixture and forming an extrudable dough by adding acid and water to the powder mixture in such amounts that the dough contains 0.8-1.2 moles acid equivalents per kg powder;
extruding the extrudable dough to form extrudates;
drying and calcining the extrudates;
impregnating the extrudates with an aqueous solution of a nickel compound;
drying, calcining and reducing the impregnated extrudates.

The invention further relates to a process for desulphurisation of a hydrocarbonaceous feedstock, wherein the feedstock is contacted with the catalyst particles as hereinbefore defined, in the presence of hydrogen, at a temperature in the range of from 150 to 500° C., a pressure in the range of from 1 to 50 bar (absolute), and a liquid velocity in the range of from 0.1 to 50 kg feedstock/litre catalyst/h.

Without being bound to any theory, it is believed that the way in which the catalyst particles of the invention are prepared results in a very high dispersion of both the alumina and the zinc oxide in the finished catalyst, resulting in very good binding properties of the alumina and in a very high availability of the zinc oxide for hydrogen sulphide absorption.

In the preparation process of the catalyst particles according to the invention, zinc oxide and alumina or an alumina precursor, both in powder form, are mixed. Preferably, pseudo boehmite is used as alumina precursor.

Acid and water are added to the powder mixture in such amounts that the mixture is peptised and that an extrudable dough is formed. In order to achieve sufficient peptising, the dough contains 0.8-1.2 moles acid equivalents, i.e. protons, per kg powder. The total amount of liquid added, i.e. acid and water, should be such that an extrudable dough is formed. It will be appreciated that the amount of liquid needed to form an extrudable dough will inter alia depend on the pore volume of the powders. Preferably, concentrated acid is used. Nitric acid, citric acid and acetic acids are examples of suitable concentrated acids. Nitric acid is preferred.

The thus-formed extrudable dough is then extruded into extrudates. The extrudates are subsequently dried and calcined. Typical drying temperatures are in the range of from 80 to 150° C.; typical calcinations temperatures in the range of from 400 to 700° C.

The calcined extrudates are impregnated with an aqueous solution of a nickel salt, preferably a basic solution of a nickel salt having a pH above the isoelectric point of alumina. More preferably the calcined extrudates are impregnated with an ammoniacal solution of a nickel salt, for example an ammoniacal solution of nickel carbonate or an ammoniacal solution of nickel hydroxide. Such an ammoniacal solution of nickel may be prepared by dissolving a nickel salt, e.g. nickel hydroxide or nickel carbonate, in a mixture of ammonia and ammonium carbonate.

An advantage of the use of an ammoniacal solution of a nickel salt is that a very high nickel dispersion can be achieved in the final catalyst particles, even on a catalyst carrier having a relatively low amount of alumina. Reference herein to nickel dispersion is to the ratio of nickel atoms at the surface of the catalyst particle as determined by hydrogen chemisorption and the total number of nickel atoms.

The impregnated extrudates are subsequently dried and calcined.

To achieve a high catalytic conversion activity for "difficult" sulphur compounds, the catalyst particles comprise nickel in a reduced valence state. Reference herein to nickel in a reduced valence state is to nickel that is essentially in metallic state, i.e. has a valence of zero. Therefore, the calcined catalyst particles are reduced prior to their use in a desulphurisation process. The calcined particles may be reduced during the catalyst preparation process, i.e. directly after the calcinations step. Since the reduced catalyst particles are pyrophoric, they have to be kept under an inert atmosphere or have to be passified until they are used in a desulphurisation reactor. Preferably, the calcined, non-reduced extrudates are loaded into a reactor for a desulphurisation process and are reduced before or during start-up of the desulphurisation process. Reduction is typically carried out in hydrogen.

The nickel is supported on a carrier comprising zinc oxide and alumina, preferably on a carrier consisting of zinc oxide and alumina, i.e. without another catalyst support material or binder present.

The Zn:Ni atomic ratio of the catalyst particles according to the invention is at least 12, preferably at least 15, more preferably at least 20. The advantage of a high Zn:Ni atomic ratio is that the catalyst has a high hydrogen sulphide absorbing capacity. The Zn:Ni ratio is, however, bound to a maximum, in order to have sufficient nickel for conversion of "difficult" sulphur compounds. The Zn:Ni atomic ratio is preferably at most 75, more preferably at most 30.

The catalyst carrier preferably comprises at most 20 weight % alumina, more preferably 5 to 15 weight % alumina. It has been found that the catalyst particles according to the invention are strong, even if the carrier has less than 20 weight % alumina. The strength of the catalyst particles is at least 80 N/cm, preferably at least 100 N/cm. The strength of the catalyst particles is measured according to ASTM D6175-98 and expressed as a force per unity of length (number-averaged length) of the catalyst particle.

The zinc oxide in the catalyst particles according to the invention has a high hydrogen sulphide absorbing capacity, in the sense that, under normal operation of the catalyst, a hydrogen sulphide absorption close to the theoretical maximum of 39.3% sulphur by weight (based on the weight of zinc oxide) can be achieved whilst the catalyst still is active for the conversion of "difficult" sulphur compounds. It has been found that an excellent nickel dispersion can be achieved by impregnating the calcined extrudates with an ammoniacal nickel solution. Thus, a relatively low amount of nickel is sufficient to result in catalyst particles showing an excellent desulphurisation performance. The catalyst particles preferably have a nickel concentration in the range of from 0.5 to 5 wt % based on the total amount of carrier, more preferably of from 1 to 4 wt %, even more preferably of from 1 to 3 wt %. The nickel dispersion in the catalyst particles according to the invention is preferably at least 20%, more preferably at least 30%.

The catalyst particles (catalyst) according to the invention can suitably be used for the desulphurisation of hydrocarbonaceous feedstocks, especially for the deep desulphurisation of hydrodesulphurisation or hydrocracking effluents that still contain "difficult-to-remove" sulphur compounds such as heterocyclic sulphur compounds.

Suitable feedstocks for the desulphurisation process of the invention are naphtha or middle distillates produced by hydrocracking or hydrodesulphurising gasoil or naphtha. These feedstocks may have a sulphur content up to 1000 ppm. The extent of sulphur reduction of the process according to the invention depends on the type of the feedstock and the sulphur content of the feedstock. For example, the sulphur content of a typical hydrodesulphurised gasoil with a sulphur content in the range of from 500 to 1000 ppmw can be reduced to a sulphur content in the range of from 20 to 100 ppmw. The sulphur content of a typical hydrocracked gasoil with a sulphur content in the range of from 10 to 50 ppmw can be reduced to a sulphur content below 1 ppmw. The sulphur content of a typical hydrocracked naphtha can be reduced to a sulphur content below 0.1 ppmw. The resulting desulphurised hydrocarbon stream is particularly suitable as feed for sulphur-sensitive processes such as steam reforming, autothermal reforming or catalytic partial oxidation.

Hydrogen should be present in the process of the invention. Hydrogen from an external source may be added to the process. Alternatively, hydrogen may be formed in-situ by dehydrogenation of part of the hydrocarbon feedstock. If hydrogen from an external source is added, the ratio of hydrogen to feedstock is preferably in the range of from 0.1 to 300 litre $H_2$ per litre feedstock, more preferably of from 0.1 to 30 litre $H_2$ per litre feedstock. In the case of in-situ hydrogen formation, the amount of hydrogen may be lower.

The process of the invention is typically operated at a temperature in the range of from 150 to 500° C., preferably of from 200 to 400° C., more preferably of from 250 to 350° C. The pressure is typically in the range of from 1 to 50 bar (absolute), and the liquid velocity in the range of from 0.1 to 50 kg feedstock/litre catalyst/h, preferably 0.1 to 10 kg feedstock/litre catalyst/h.

EXAMPLES

The invention will be further illustrated by means of the following illustrative examples that are exemplary and are not intended as limitations on the scope of the invention.

Example 1

According to the Invention

Catalyst Preparation 4952 g of ZnO powder (ex. Durham; Activox C80; loss-on-ignition of 3.7% wt: 4769 g of dry ZnO) was mixed with 726 g pseudo boehmite powder (ex. Criterion; loss-on-ignition of 27% wt: 530 g on dry base) in a Simpson mix muller. To this mixture, 371 g concentrated (65 wt %) nitric acid, 2203 g of water and extrusion aids were added. The resulting mixture was kneaded for 30 minutes to form an extrudable dough. The dough was extruded using 1.3 mm tri-lobe shaped dies on a Bonnot extruder. The extrudates were dried at 120° C. for 2 hours and calcined at 550° C. for 2 hours. The strength of the extrudates were measured as 107 N/cm.

An ammoniacal nickel impregnation solution was prepared by adding 200 g ammonium carbonate to 600 g ammonia (25 wt %). To this mixture, 300 g $NiCO_3$ (ex. OMG; 47.6 wt % Ni) was added. While stirring, the mixture was slowly heated to 40° C. until a solution was obtained.

The extrudates were impregnated with the nickel impregnation solution. The impregnated extrudates were subsequently dried at 120° C., calcined at 350° C. during 2 hours.

The catalyst particles contained 5.3 wt % Ni (calculated as metallic Ni) on a carrier of 90 wt % ZnO and 10 wt % alumina. The nickel dispersion was 30%. The sulphur absorption capacity of the ZnO was 30 weight %.

Desulphurisation

The calcined catalyst particles were loaded into a desulphurisation reactor and reduced by leading a flow of hydrogen (30 Nl/h) over the particles at a pressure of 2 bar (absolute). During the reduction the temperature was maintained at 120° C. for 2 hours, then increased to 370° C. at which it was maintained for 2 hours. The temperature was then decreased to 300° C., the pressure increased to 15 bar (absolute), and a hydrocracked gasoil having a sulphur content of 18 ppmw and hydrogen (3 Nl/kg oil) were led over the catalyst particles. The sulphur content of the thus-treated gasoil was below 0.1 ppmw.

Example 2

According to the Invention

A catalyst carrier comprising 85 wt % ZnO and 15 wt % alumina was prepared with the same preparation method as described in EXAMPLE 1. The strength of the extrudates were measured as 130 N/cm. The extrudates were impregnated with a nickel solution as described in EXAMPLE 1 resulting in a nickel concentration of 4.8 wt % (calculated as metallic Ni) based on the weight of the carrier. The nickel dispersion was 41%.

Example 3

Comparative

A catalyst carrier of 100 wt % ZnO and no alumina was prepared with the same preparation method as described in EXAMPLE 1. The strength of the extrudates was less than 20 N/cm.

Example 4

Comparative

As a comparison, a catalyst was prepared wherein the nickel precursor was added to the extrudable dough. To a mixture of ZnO powder and pseudo boehmite powder, concentrated nitric acid, water, a nickel nitrate solution and extrusion aids were added to form an extrudable dough. The preparation of the extrudable dough was as described in EXAMPLE 1, except that part of the water was replaced by a nickel nitrate solution. The dough was extruded, dried and calcined as described in EXAMPLE 1. The resulting extrudates comprised 90 wt % ZnO, 10 wt % alumina and 6.8 wt % nickel (calculated as metallic Ni) based on the weight of ZnO and alumina. The strength of the extrudates was 30 N/cm.

The catalyst composition and the strength of the catalyst particles is shown in table 1 for the catalysts of EXAMPLES 1 to 4. It can be seen that the catalysts prepared according to the catalyst preparation method of the invention (EXAMPLES 1 and 2) have a high strength and a high nickel dispersion. The comparative catalyst of EXAMPLE 4 with a similar overall composition as the catalyst of EXAMPLE 1, but not prepared according to the method of the invention has a much lower strength. EXAMPLE 3 shows that catalyst particles without alumina have a very low strength.

TABLE 1

Catalyst composition and strength of catalyst particles

| EXAMPLE | ZnO (wt %) | alumina (wt %) | Ni (wt %) | Ni dispersion (%) | strength (N/cm) |
|---|---|---|---|---|---|
| 1 (invention) | 90 | 10 | 5.3 | 30 | 107 |
| 2 (invention) | 85 | 15 | 4.8 | 41 | 130 |
| 3 (comparison) | 100 | 0 | — | — | <20 |
| 4 (comparison) | 90 | 10 | 6.8 | | 30 |

Example 5

In order to test the sulphur absorbing capacity of the catalyst particles of the invention, a desulphurisation experiment was carried out with a hydrodesulphurized gasoil with a relatively high amount of sulphur compounds.

21.6 gram of catalyst particles prepared according to EXAMPLE 2 were loaded into a reactor tube. The catalyst was reduced at atmospheric pressure in a flow of 10 Nl/hr $H_2$ by increasing the temperature to 370° C. at a rate of 20° C./h. The reduced catalyst was cooled down to 350° C., the reactor was pressurized to 20 barg with $H_2$ and a hydrodesulphurized gasoil containing sulphur compounds corresponding to 750 ppm by weight S (initial boiling point 142° C., final boiling point 441° C.) was introduced at a rate of 2 gram oil/gram catalyst/h and the hydrogen flow was 500 Nl $H_2$/kg oil. The reactor effluent was de-pressurized and the atmospheric liquid product was recovered over a period of time. Table 2 below shows the sulphur content of the recovered liquid at different periods of time.

TABLE 2

Sulphur content of desulphurised gasoil

| Period of time (hours after start) | S content of recovered liquid (ppmw) |
|---|---|
| 6-9 | 5 |
| 28-31 | 4 |
| 100-103 | 14 |
| 124-127 | 16 |
| 240-244 | 173 |

After approximately 260 hours, the experiment was terminated. The sulphur content of the spent catalyst was 25.5% by weight based on the weight of the catalyst (theoretical value for 100% conversion of the ZnO to ZnS would be 27.1% S by weight), indicating that the ZnO in the catalyst particles according to the invention has a high hydrogen sulphide absorbing capacity.

I claim:

1. A catalyst comprising nickel in a reduced valence state on a carrier comprising zinc oxide and alumina, wherein the Zn:Ni atomic ratio is at least 12, and the catalyst is prepared by:
   mixing zinc oxide in the form of a powder and alumina or an alumina precursor in the form of a powder thereby providing a powder mixture;
   peptising the powder mixture and forming an extrudable dough by adding acid and water to the powder mixture in such amounts that the dough contains 0.8-1.2 moles acid equivalents per kg powder thereby providing an extrudable dough;
   extruding the extrudable dough to form extrudates;
   drying and calcining the extrudates;
   impregnating said calcined extrudates with an aqueous solution of a nickel compound thereby providing an impregnated extrudate;
   drying, calcining and reducing the impregnated extrudates.

2. The catalyst of claim 1 wherein the acid is nitric acid, citric acid or acetic acid.

3. The catalyst of claim 1 wherein the aqueous solution of the nickel compound is an ammoniacal solution of a nickel salt.

4. The catalyst of claim 2 wherein the aqueous solution of the nickel compound is an ammoniacal solution of a nickel salt.

5. The catalyst of claim 1 wherein the carrier comprises zinc oxide and alumina.

6. The catalyst of claim 3 wherein the carrier comprises zinc oxide and alumina.

7. The catalyst of claim 1 wherein the Zn:Ni atomic ratio is at least 15, and wherein the Zn:Ni atomic ratio is at most 75.

8. The catalyst of claim 1 wherein the Zn:Ni atomic ratio is at least 20, and wherein the Zn:Ni atomic ratio is at most 75.

9. The catalyst of claim 1 wherein the Zn:Ni atomic ratio is at least 15, and wherein the Zn:Ni atomic ratio is at most 30.

10. The catalyst of claim 1 wherein the carrier comprises at most 20 weight % alumina.

11. The catalyst of claim 3 wherein the carrier comprises at most 20 weight % alumina.

12. The catalyst of claim 5 wherein the carrier comprises at most 20 weight % alumina.

13. The catalyst of claim 7 wherein the carrier comprises at most 20 weight % alumina.

14. The catalyst of claim 1 wherein the carrier comprises from 5 to 15 weight % alumina.

15. The catalyst of claim 1 having a strength of at least 80 N/cm.

16. The catalyst of claim 10 having a strength of at least 80 N/cm.

17. The catalyst of claim 1 having a strength of at least 100 N/cm.

18. The catalyst of claim 1 wherein the nickel concentration is in the range of from about 0.5 to about 5 wt % based on the total weight of carrier.

19. The catalyst of claim 3 wherein the nickel concentration is in the range of from about 0.5 to about 5 wt % based on the total weight of carrier.

20. The catalyst of claim 1 wherein the nickel concentration is in the range of from 1 to 4 wt % based on the total weight of carrier.

21. The catalyst of claim 1 having a nickel dispersion of at least 20%.

22. The catalyst of claim 3 having a nickel dispersion of at least 20%.

23. The catalyst of claim 10 having a nickel dispersion of at least 20%.

24. The catalyst of claim 15 having a nickel dispersion of at least 20%.

25. The catalyst of claim 1 having a nickel dispersion of at least 30%.

26. The catalyst of claim 21 having a nickel dispersion of at least 30%.

* * * * *